United States Patent
Hanson et al.

(10) Patent No.: US 9,604,237 B2
(45) Date of Patent: Mar. 28, 2017

(54) PITCH-BASED CONTROL FOR SPRAYERS AND SPRAYER OPERATIONS

(71) Applicant: DEERE & COMPANY, Moline, IL (US)

(72) Inventors: David A. Hanson, Urbandale, IA (US); Richard A. Humpal, Ankeny, IA (US); Bradley J. Hitchler, Baxter, IA (US); Matthew T. Martin, Ankeny, IA (US)

(73) Assignee: DEERE & COMPANY, Moline, IL (US)

( * ) Notice: Subject to any disclaimer, the term of this patent is extended or adjusted under 35 U.S.C. 154(b) by 216 days.

(21) Appl. No.: 14/485,052

(22) Filed: Sep. 12, 2014

(65) Prior Publication Data

US 2016/0074891 A1 Mar. 17, 2016

(51) Int. Cl.
| | |
|---|---|
| *G01F 17/00* | (2006.01) |
| *B05B 12/08* | (2006.01) |
| *A01M 7/00* | (2006.01) |
| *A01C 23/00* | (2006.01) |
| *G01F 23/00* | (2006.01) |
| *G01B 21/22* | (2006.01) |

(Continued)

(52) U.S. Cl.
CPC ............ *B05B 12/08* (2013.01); *A01C 23/007* (2013.01); *A01M 7/0085* (2013.01); *A01M 7/0089* (2013.01); *G01B 21/22* (2013.01); *G01F 23/0076* (2013.01); *A61B 5/1073* (2013.01); *G01F 17/00* (2013.01); *G01F 22/02* (2013.01); *G01F 23/14* (2013.01); *G01F 23/26* (2013.01); *G01N 9/02* (2013.01)

(58) Field of Classification Search
CPC ........................................................ G01F 17/00
USPC ............................................................. 73/149
See application file for complete search history.

(56) References Cited

U.S. PATENT DOCUMENTS

| | | | | |
|---|---|---|---|---|
| 3,726,140 A | * | 4/1973 | Barbee | ................... G01F 23/14 73/299 |
| 4,015,366 A | * | 4/1977 | Hall, III | ............... A01D 46/005 137/236.1 |

(Continued)

FOREIGN PATENT DOCUMENTS

| | | | | |
|---|---|---|---|---|
| FR | 2976071 A1 | 12/2012 | | |
| IT | WO2006032309 | * | 5/2005 | ............. G01F 23/26 |
| WO | 2006032309 A1 | 3/2006 | | |

OTHER PUBLICATIONS

European Search Report, 'EP15181907', European Patent Office EPO, sheets 1-3.*

(Continued)

*Primary Examiner* — Clayton E LaBalle
*Assistant Examiner* — Kevin Butler
(74) *Attorney, Agent, or Firm* — Taft Stettinius & Hollister LLP; Stephen F. Rost (57) ABSTRACT

A computer-implemented method and a control system are described for controlling one or more operations of a sprayer vehicle with a tilt-detection mechanism, a tank, and a tank fill-volume sensor. The tilt-detection mechanism is utilized to determine a tilt indicator. A tilt value is determined based upon the tilt indicator. A tank fill-volume indicator is determined based upon information from the tank fill-volume sensor. A tilt-corrected fill-volume of the tank is determined based upon the tilt value and the tank fill-volume indicator.

18 Claims, 3 Drawing Sheets

(51) Int. Cl.
*A61B 5/107* (2006.01)
*G01F 23/14* (2006.01)
*G01N 9/02* (2006.01)
*G01F 23/26* (2006.01)
*G01F 22/02* (2006.01)

(56) References Cited

U.S. PATENT DOCUMENTS

| | | | | |
|---|---|---|---|---|
| RE31,023 E | * | 9/1982 | Hall, III | A01D 46/24 137/236.1 |
| 5,072,615 A | * | 12/1991 | Nawrocki | G01F 23/0076 33/366.14 |
| 5,138,559 A | * | 8/1992 | Kuehl | G01F 23/14 340/618 |
| 5,309,764 A | | 5/1994 | Waldrop et al. | |
| 5,351,725 A | | 10/1994 | Suthergreen et al. | |
| 5,665,895 A | * | 9/1997 | Hart | G01F 1/007 702/100 |
| 6,029,514 A | * | 2/2000 | Adam | G01F 23/0038 73/149 |
| 6,253,607 B1 | * | 7/2001 | Dau | G01D 3/032 73/290 R |
| 6,615,656 B1 | | 9/2003 | Breed et al. | |
| 6,666,085 B1 | | 12/2003 | Lowe | |
| 6,892,572 B2 | | 5/2005 | Breed et al. | |
| 7,891,242 B2 | * | 2/2011 | Cheng | G01C 9/06 73/304 R |
| 8,401,761 B2 | | 3/2013 | Bohr et al. | |
| 9,297,686 B1 | * | 3/2016 | Ross, Jr. | G01F 23/292 |
| 2003/0033871 A1 | * | 2/2003 | Carroll | G01F 23/14 73/299 |
| 2003/0217596 A1 | * | 11/2003 | Dirksen | G01F 23/0023 73/149 |
| 2007/0215722 A1 | * | 9/2007 | Smith | A01C 23/042 239/398 |
| 2008/0314674 A1 | * | 12/2008 | Kamio | B62J 27/00 180/282 |
| 2009/0056437 A1 | * | 3/2009 | Kawanishi | G01F 23/14 73/295 |
| 2011/0010070 A1 | * | 1/2011 | Bohr | G01F 23/0076 701/102 |
| 2011/0270542 A1 | * | 11/2011 | Chappell | G01F 23/0076 702/55 |
| 2012/0234074 A1 | * | 9/2012 | Hagen | G01F 1/32 73/1.73 |
| 2013/0074595 A1 | * | 3/2013 | Muyskens | G01F 23/0076 73/304 C |
| 2014/0183276 A1 | * | 7/2014 | Kroese | A01C 23/008 239/74 |
| 2015/0143898 A1 | * | 5/2015 | Wiebe | G01F 25/0061 73/299 |
| 2016/0074891 A1 | * | 3/2016 | Hanson | A01M 7/0085 239/74 |
| 2016/0150771 A1 | * | 6/2016 | Tollefsrud | A01M 7/0089 239/172 |

OTHER PUBLICATIONS

Vern Hofman et al. 'AE-73 Spray Equipment and Calibration', Agricultural and Biosystems Engineering North Dakota State University, Aug. 1, 2014, p. 9.*
European Search Report, dated Feb. 8, 2016, pp. 1-7.

* cited by examiner

PITCH-BASED CONTROL FOR SPRAYERS AND SPRAYER OPERATIONS

CROSS-REFERENCE TO RELATED APPLICATION(S)

Not applicable.

STATEMENT OF FEDERALLY SPONSORED RESEARCH OR DEVELOPMENT

Not applicable.

FIELD OF THE DISCLOSURE

This disclosure relates to control of spraying operations in a sprayer vehicle, including tank filling, tank mixing, spray application, and other operations.

BACKGROUND OF THE DISCLOSURE

In various settings, it may be useful to provide a sprayer vehicle for spraying various liquids and liquid solutions over agricultural (or other) areas. Typical sprayer vehicles may include one or more tanks, which may be filled with various substances, as well as various spraying devices for dispersing the contents of the tank(s) during a spray application.

In various operations, it may be useful to determine the volume of a substance in a tank (i.e., the tank "fill-volume") with a relatively high precision. For example, certain spraying operations may utilize mixtures of relatively precise composition, which must be pre-mixed within the sprayer tank by adding various chemicals (e.g., various powdered chemicals) to one or more carrier liquids (e.g., water). Accordingly, in order to ensure appropriate mixture composition, it may be useful to know the fill-volume of a carrier with relatively high accuracy. Similarly, knowledge of precise tank fill-volumes may ensure that sufficient liquid (or other substance) is provided to cover the entire area to be sprayed, as well as allowing more accurate tracking of chemical dispersal over a field. To this end, various devices may be provided to measure an indicator of substance volume. For example, sight tubes may be provided on sprayer tanks in order to allow an operator to visually assess fill-volume. Likewise, devices such as load cells or float sensors may provide more automated measurements of tank fill-volumes.

In various instances, however, a sprayer vehicle may be oriented with various degrees of tilt. For example, if a vehicle stops on contoured or slanted terrain for a filling or mixing operation, or drives over contoured or slanted terrain for a spraying operation, the vehicle may experience various degrees of pitch or roll. As used herein, the "pitch" of a vehicle may refer to a rotation of the vehicle about an axis extending along a lateral fore-aft centerline of the vehicle, as would correspond to inclination or declination of the vehicle in the forward and reverse directions of travel, or the fore and aft of the vehicle when stationary. The "roll" of a vehicle, in contrast, may correspond to side-to-side vehicle rotation about a longitudinal centerline of the vehicle. It will be understood that tilt may adversely affect the accuracy of known devices for measuring fill-volume, potentially resulting in sub-optimal accuracy in fill-volume assessments.

SUMMARY OF THE DISCLOSURE

A control system and computer-implemented method are disclosed for controlling aspects of sprayer operations, including tank filling, mixing of different liquids or other substances, and spray-application operations.

According to one aspect of the disclosure, a computer-implemented method is applied with respect to a sprayer vehicle with a tilt-detection mechanism, a tank, and a tank fill-volume sensor. The tilt-detection mechanism is utilized to determine a tilt indicator and at least one tilt value is determined based upon the tilt indicator. A tank fill-volume indicator is determined based upon information from the tank fill-volume sensor. A tilt-corrected fill-volume of the tank is determined based upon the tilt value and the tank fill-volume indicator.

In certain embodiments, the at least one tilt value includes a pitch value and a roll value. A roll- or pitch-corrected fill-volume estimate may be determined based upon the tank fill-volume indicator and, respectively, the roll or pitch value. A pitch- or roll-based fill-volume correction may be determined based upon the tank fill-volume indicator and, respectively, the pitch or roll value. The tilt-corrected fill-volume may then be determined based upon subtracting the pitch- or roll-based correction from, respectively, the roll- or pitch-corrected estimate.

In certain embodiments, the tank may receive a primary substance during a primary fill operation and the tilt-corrected fill-volume is determined to represent, at least in part, an amount of primary substance in the tank. An indicator of the tilt-corrected fill-volume is provided after the primary fill operation and an amount of secondary substance is received, in a secondary fill operation, with the amount of secondary substance being determined based upon the tilt-corrected fill-volume indicator.

In certain embodiments, an indicator of the tilt-corrected fill-volume may be provided to a material-management system to manage one or more aspects of at least one of a tank-filling, a tank-mixing, and a spray application. A pumping operation for filling the tank may be controlled based upon the tilt-corrected fill-volume.

According to another aspect of the disclosure, a control system includes one or more processor devices and one or more memory architectures coupled with the one or more processor devices. The one or more processor devices may be configured to execute various aspects of the method summarized above, as well as various other functionality.

The details of one or more implementations of the disclosure are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION

The following describes one or more example implementations of the disclosed system and method, as shown in the accompanying figures of the drawings described briefly above.

As noted above, it may be useful to determine the volume of liquid (or other substance) in a sprayer tank with relatively high precision. For example, if a sprayer tank is to be filled with a carrier liquid (e.g., water), and a secondary substance (e.g., pesticide, herbicide, or fertilizer) is to be diluted to a particular concentration in the carrier liquid, it may be useful to know the volume of carrier liquid in the tank with relatively high precision in order to determine the appropriate volume (or weight) of secondary substance to be added. Similarly, in cases where a material (or other) management system is to be used to track the application of a substance (e.g., an herbicide mixture) at various field locations (or to track other aspects of sprayer operation), it may be useful to provide to such a system a relatively precise measure of how much of the substance is present in a sprayer tank at various times. (Various examples discussed herein may address liquid levels in a sprayer tank. It will be understood, however, that the principles disclosed herein may also be applied in tanks for non-liquid substances.)

As also noted above, determination of the volume of substance in a tank (i.e., tank "fill-volume") may be complicated by operation of a vehicle (e.g., a sprayer vehicle) on non-level terrain. (It will be understood that "operation" as used herein, may include use of a vehicle in stationary applications, such as in a tank-filling or tank-mixing operation.) This may result, for example, because various degrees of tilt of a vehicle may result in tilting of the vehicle's tank. If a sensor or other device directed toward the volume of substance within a tank (e.g., a level sensor within the tank, a load sensor, a sight tube, and so on) has been calibrated for level operation, this tilting may result in relatively reduced accuracy for substance volumes that are determined from such a sensor or device. For example, if a float sensor is provided for measuring liquid height within a sprayer tank, and the tank is tilted away from its normal orientation, the level (i.e., height) of liquid measured by the float sensor may not accurately map to the actual liquid volume within the tank. This may be particularly true at higher degrees of tilt, and in tanks with complex geometry (e.g., because liquid may tend to pool in various internal cavities of the tank). In order to address this and other issues, a pitch-based sprayer control ("PBSC") method or similar control system, is disclosed herein.

In certain embodiments, under a PBSC method, a model (e.g., a numerical model) or look-up table relating tank volume to a separate, measured quantity may be determined. For example, for a tank employing a float-style (or other) level sensor, numerical (or other) modeling of the tank may allow the determination of a polynomial (or other) relationship between the sensed fill level of a tank (e.g., the height of liquid in the tank as measured by the level sensor), the tilt of the tank (e.g., pitch and roll, which may generally correspond to the pitch and roll of the associated vehicle), and actual fill-volume of the tank (e.g., actual liquid volume within the tank). In level operation, the level sensor may provide a relatively accurate indicator of liquid volume within the tank (e.g., through an appropriately correlated relationship between liquid level sensed by the sensor, and the actual fill-volume). During non-level operation, however, tilt of the tank (e.g., by virtue of similar tilt of the sprayer vehicle) may cause liquid to over-fill various portions of the tank, which may detrimentally affect the correlation between the level sensed by the level sensor and the actual volume of liquid in the tank. A PBSC method may utilize the above-noted numerical (or other) model to correct the liquid volume accordingly. For example, an on-board (or other) controller for the associated sprayer vehicle may receive a measurement (or other indicator) of vehicle tilt, as well as a reading from the level sensor. The controller may then input these values into the numerical (or other) tank model (or use the values to reference an appropriate look-up table) in order to determine a tilt-corrected volume of the liquid in the tank.

The tilt-corrected volume, as determined by a PBSC method, may then inform various sprayer operations. For example, the tilt-corrected volume may guide a filling operation, allowing a tank to be filled to a relatively precise level even on uneven terrain. Similarly, the tilt-corrected volume may guide a mixing operation. For example, if a tank has been filled with a primary substance (e.g., a carrier liquid such as water), the tilt-corrected volume of the primary substance may be utilized to guide addition (and mixing) of a secondary substance that is to be diluted therein (e.g., a powdered or liquid pesticide, herbicide, or fertilizer). Further, a tilt-corrected volume may be provided to various material-management systems to allow for detailed and accurate tracking of material usage, dispersal locations, and so on.

It will be understood that sensors of other types may be employed for a particular sprayer as an alternative (or in addition) to the level sensor noted in the example above. As such, one or more other sensor types that measure values relating to tank fill-volumes may be utilized to determine one or more inputs to a PBSC method. For example, certain sprayers may be equipped with load sensors at various locations beneath the sprayers' tanks. As with level sensors, such load sensors may provide lower-accuracy assessment of liquid levels when the relevant sprayers are operating on tilted terrain. For example, if vehicle tilt causes liquid within a tank to pool in a location removed from the associated load sensor(s), the sensor(s) may indicate a lower-than-actual load of liquid for the tank, which may result in calculation of a lower-than-actual liquid volume for the tank. As with a level sensor, however, measurements from such a load sensor may be utilized in a PBSC method in order to determine a corrected assessment of liquid (or other fill) volume for the tank.

Figure 1:
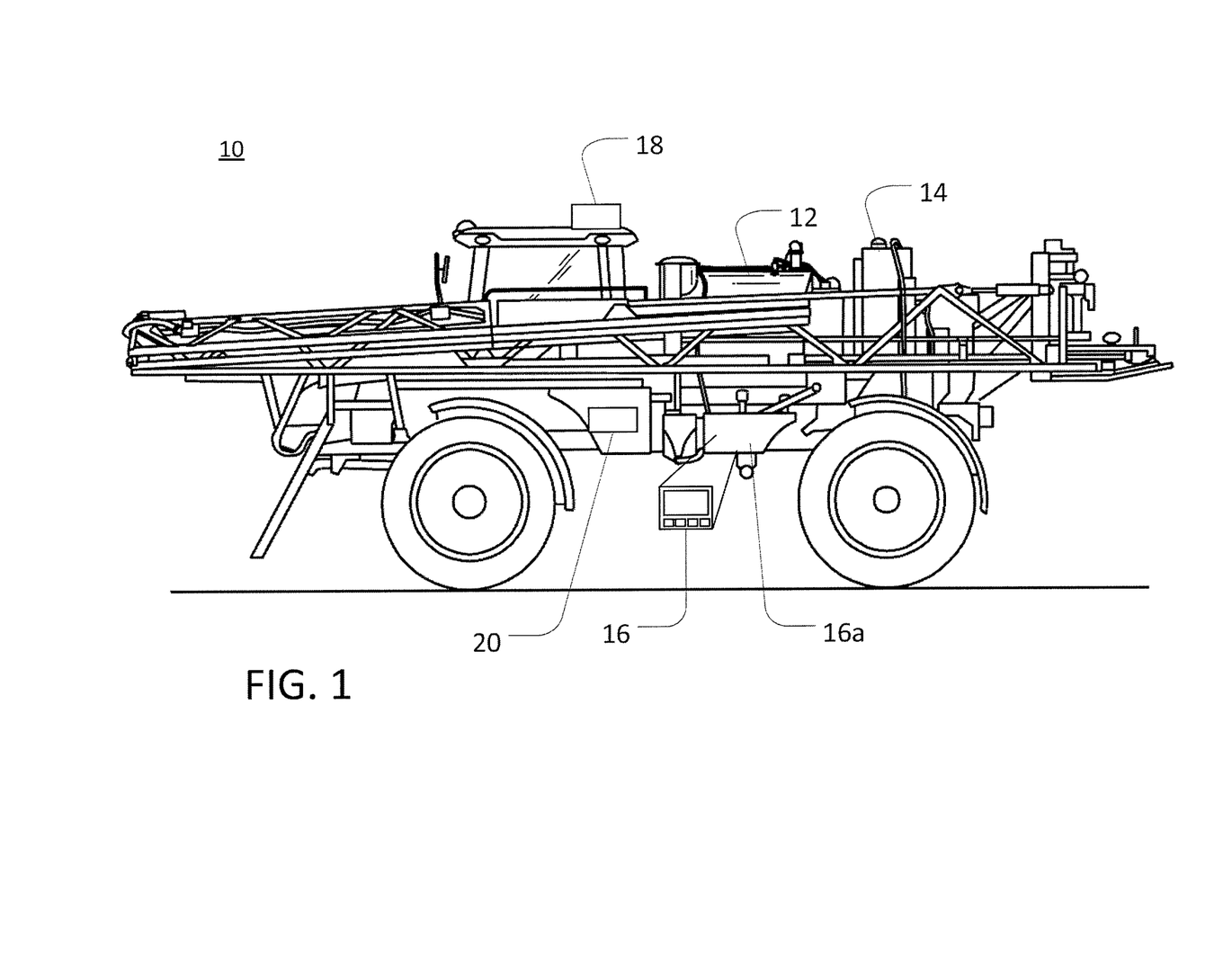
FIG. 1 is a side view of an example sprayer vehicle with respect to which the disclosed system and/or method may be implemented.

Referring now to FIG. 1, a PBSC method may be implemented with respect to a variety of vehicles, including example sprayer 10. Sprayer 10 (or other sprayers) may include one or more primary tanks, such as tank 12, for storage, mixing, and dispersal of various substances (e.g., various liquids). Sprayer 10 may also include one or more secondary tanks, such as tank 14, which may store one or more additional substances to be added to tank 12 as desired or otherwise mixed with the substance in tank 12 for a spraying operation. Tanks 12 and 14 may be designed in various known ways and from various known materials, including stainless steel or other metals, or various polymer materials.

Sprayer 10 may include various screens or other display devices. For example, display 16 (shown removed from protective panel 16a), or another output interface, may provide an active display to indicate a current fill-volume of tank 12 at various times. Similar displays and other output interfaces (not shown) may also be provided, including within the cab of sprayer 10. Display 16, which may be an LCD or other device, may be in communication with controller 20 (which may include various processors, memory architectures, programmable electronic circuits, and so on), or with various other computing devices and systems (e.g., a CAN bus of sprayer 10) (not shown).

Sprayer 10 may also include tilt sensor 18, which may be configured to determine the pitch and roll of sprayer 10 (or an indicator thereof) and provide a signal representing that pitch and roll (or the indicator thereof) to controller 20 or another computing device (e.g., via a CAN bus (not shown) of sprayer 10). In certain embodiments, tilt sensor 18 may measure various indicators of tilt, rather than measuring tilt directly. For example, tilt sensor 18 may include one or more accelerometers, which may measure various acceleration values, or may include various other devices for measuring various other tilt-related values. Tilt sensor 18 may then utilize these indicator values itself in order to determine an actual tilt of the sprayer, or may transmit them to another computing device, such as controller 20, for a similar operation.

In certain embodiments, tilt sensor 18 may include a multi-axis (e.g., three-axis) accelerometer, in which case a pitch value for sprayer 10 may sometimes be determined directly from the accelerometer measurements. For example, certain GPS devices included in various vehicles (e.g., various tractors) may include various accelerometers (e.g., one or more tri-axial accelerometers) which may be utilized as part of determining a vehicle pitch. Other devices may also be utilized, including in various combinations. For example, certain embodiments may utilize gyroscopes, fluid-based devices (including fluid-based accelerometers), or other measurement devices to determine vehicle tilt, or tilt indicators.

In certain implementations, accelerometer measurements from tilt sensor 18 may be combined with other information in order to determine a tilt value for sprayer 10 (i.e., tilt sensor 18 may determine various tilt-related values, which may be utilized in combination with other values, or by other devices, to derive the actual vehicle tilt). For example, in certain implementations, a forward/reverse acceleration value for sprayer 10 may be determined based upon determining a wheel speed of the sprayer, then computing a derivative of the determined wheel speed (i.e., the wheel-based acceleration). Assuming little or no wheel slippage (or taking into account the degree of wheel slippage), this acceleration may then be appropriately subtracted from an acceleration value determined based upon accelerometer measurement (e.g., from tilt sensor 18), in order to remove from the determined acceleration value the acceleration resulting from actual forward/reverse vehicle acceleration. The remaining acceleration value, accordingly, may be utilized (along with the known acceleration of gravity) to determine an appropriate tilt value for the vehicle.

It will be understood, that sprayer 10 may undergo significant amounts of tilt (e.g., 15 degrees or more) during certain operations (including stationary operations). Accordingly, it will be understood that tilt sensor 18 may be selected in order to provide relatively high accuracy tilt measurement over a wide range of potential tilt values.

In certain embodiments, one or more float (or other) sensors may be utilized within tank 12 in order to provide a measurement of liquid levels within the tank. For example, referring also to FIGS. 2A and 2B, generally rounded stainless steel tank 12a or complex polymer tank 12b may be utilized on sprayer 10. Tanks 12a and 12b may include, respectively, level sensors 30a and 30b (shown removed from tanks 12a and 12b, for clarity of presentation). Sensors 30a and 30b (or other tank sensors) may be generally centered within their respective tanks, or may be oriented in other locations. In either of sensors 30a and 30b, a float (e.g., float 32a or 32b) may ride along a vertical (or other) guide (e.g., guide 34a or 34b), with sensors 30a and 30b providing an output voltage (or other signal) depending on the position of float 30a or 30b on guide 34a or 34b. In this way, for example, sensors 30a and 30b may provide a signal to controller 20 (or another computing device), which may indicate the respective measured level of liquid within tanks 12a and 12b.

Figure 2A:
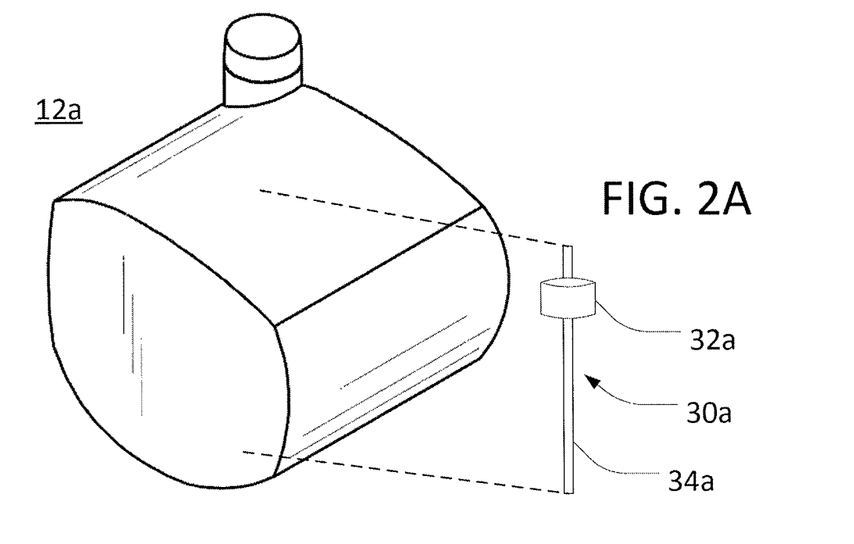
FIG. 2A is a perspective view of a sprayer tank and associated components for use with the example vehicle of FIG. 1.
Figure 2B:
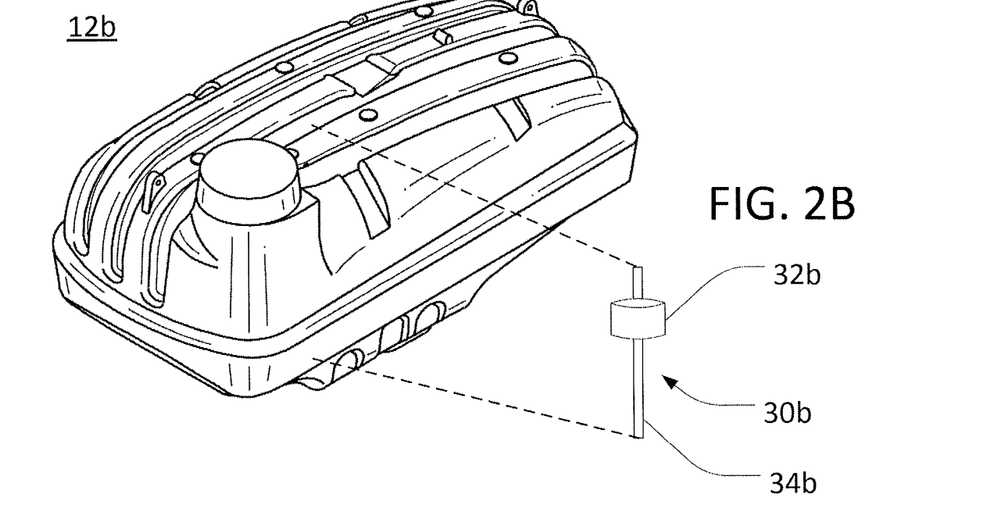
FIG. 2B is a perspective view of another sprayer tank and associated components for use with the example vehicle of FIG. 1.

Sensors 30a and 30b may be generally calibrated with respect to level operation of sprayer 12, such that the level-indicating output signal (e.g., the voltage) provided by the sensors may be directly converted to a fill-volume for the associated tank. However, if tanks 12a and 12b are subjected to tilt (e.g., to varying degrees of pitch or roll), the liquid level indicated by the position of floats 32a and 32b may no longer correspond to a liquid level that is indicative of the actual fill-volume of tanks 12a and 12b. Accordingly, unless appropriate correction is applied, the signal provided by sensors 30a and 30b to controller 30 may correlate to a fill-volume that does not accurately represent the amount of liquid within tanks 12a and 12b. In certain implementations, and at expected degrees of tilt, this error may amount to 50 gallons or more (e.g., for a 1200 gallon tank), which could lead to significant inaccuracies in mixing (or other) operations.

Figure 3:
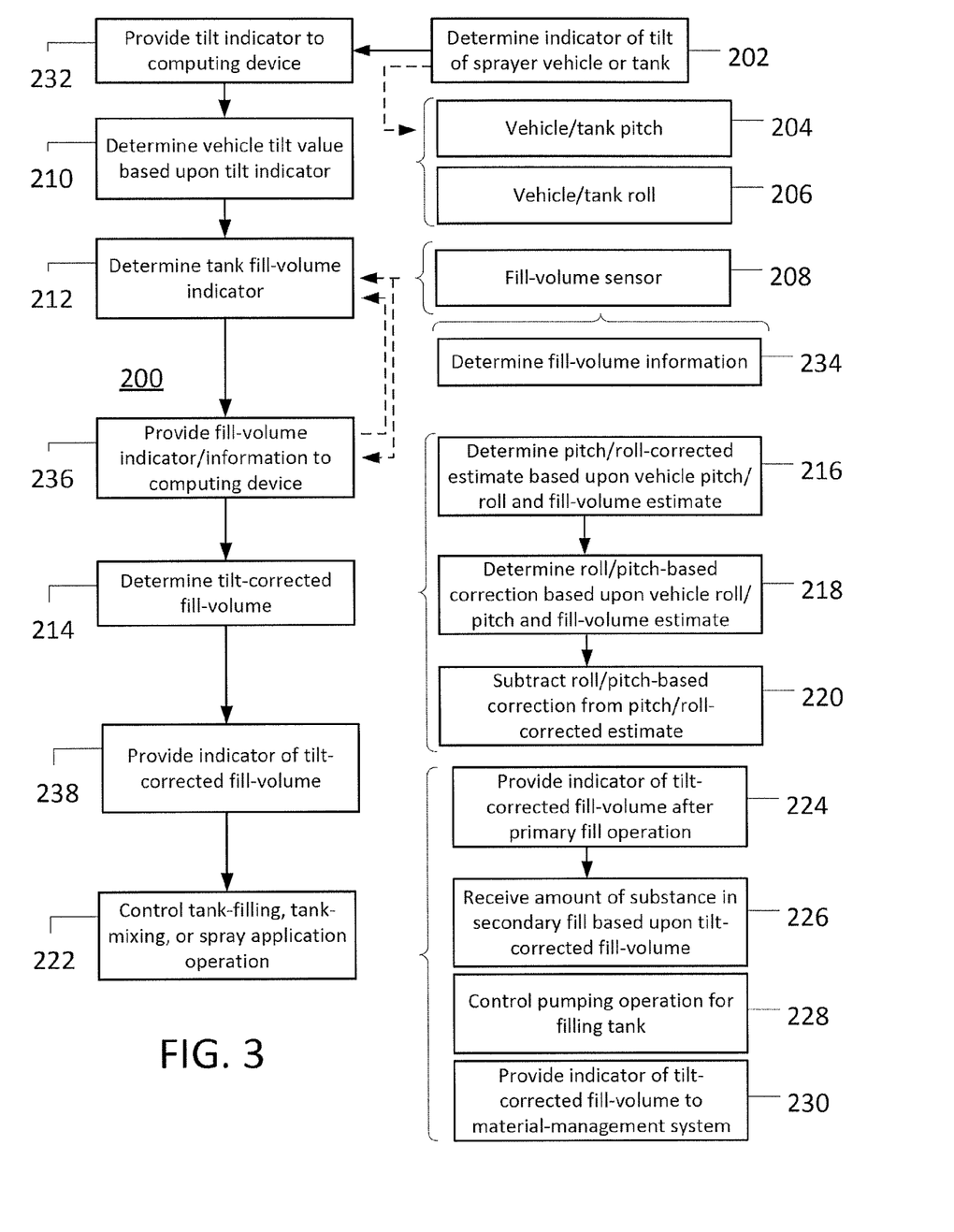
FIG. 3 is a process diagram associated with a method for controlling aspects of tank-filling, tank-mixing, or other spraying operations for the example vehicle of FIG. 1.

Accordingly, and referring also to FIG. 3, a PBSC method, such as method 200, may be applied. In certain embodiments, method 200 may be applied for a sprayer vehicle including a tilt-detection mechanism (e.g., tilt sensor 18), a tank (e.g., tank 12), and a tank sensor (e.g., float sensor 30a).

In certain embodiments, instruction sets and subroutines representing a PBSC method (e.g., PBSC method 200) may be stored on storage device forming part of (or otherwise coupled to) controller 20, and may be executed by one or more processors and one or more memory architectures (e.g., as included in or associated with controller 20). In certain implementations, a PBSC method (e.g., PBSC method 200) may be a stand-alone method. In certain implementations, a PBSC method may operate as part of, or in conjunction with, one or more other methods or processes and/or may include one or more other methods or processes. Likewise, in certain implementations, a PBSC method may be represented and implemented by an entirely hardware-based configuration, in addition or as an alternative to a configuration having a PBSC method as a set of instructions stored in a storage device (e.g., a storage device included in or associated with controller 20). For the following discussion, PBSC method 200 will be described for illustrative purposes. It will be understood, however, that other configurations may be possible.

With respect to sprayer 10, with which PBSC method 200 may be associated (and within which it may be stored or executed), PBSC method 200 may include determining 202 an indicator of a tilt of sprayer 10 and determining 210 a tilt value based upon the determined 202 tilt indicator. In certain embodiments, PBSC method 200 may include determining 202 an indicator of a degree of pitch 204 or roll 206 of sprayer 10 by way of tilt sensor 18. For example, tilt sensor 18 may detect a degree of acceleration of sprayer 10 (e.g., as discussed in greater detail above), which may then be converted to an indicator of vehicle pitch 204 and roll 206 in order to assist in determining 210 the tilt value. In certain implementations, the tilt sensor 18 may then provide 232 the determined 202 tilt indicator to a computing device (e.g., the controller 20). (In this and other aspects, information may be communicated between various components of the sprayer 10 (and other platforms) through wired connections, through wireless transmissions, or otherwise.)

Other means of determining 210 the tilt value may also be employed. Further, in certain embodiments, a tilt-detection mechanism (e.g., tilt sensor 18) may determine 210 a tilt value with or without the assistance of a separate computing device. For example, tilt sensor 18 may determine 202 voltage signals representing various degrees of acceleration of sprayer 10 and may itself determine 210 a tilt of sprayer 10 based upon those signals (e.g., with an included computing device, such as a processor and memory architecture, a programmable electronic circuit, and so on). (Likewise, various devices not limited to sensor 18 and controller 20 may work independently, in conjunction, or otherwise, with respect to this or various other aspects of method 200).

Method 200 may further include determining 212 a tank fill-volume indicator based upon information from fill-volume sensor 208. The fill-volume sensor 208 may determine 234 fill volume information in a variety of ways. In certain implementations, for example, fill-volume sensor 208 may not necessarily measure the actual fill-volume of liquid (or other substance) in tank 12, but may detect a related value such as liquid height within the tank, local liquid weight, local liquid pressure, and so on. In certain implementations, this determined 234 information may be provided 236 to a computing device (e.g., a computing device included in the sensor 208 or a separate controller or other device), which may then determine 212 a tank fill-volume indicator. In certain implementations, the fill-volume sensor 208 (e.g., via an included computing device) may itself determine 212 a fill-volume indicator, then provide 236 this indicator to another device.

In an example operation, a level sensor for tank 12 (e.g., a float sensor, such as float sensor 30a) may provide fill-volume information in the form of a voltage indicator that correlates to the height of liquid within tank 12, as sensed by the level sensor. After appropriate calibration of such a level sensor (or other sensor 208), and during level (i.e., non-tilted) operation of sprayer 10, the output of the sensor (e.g., the output voltage) may then be converted to an estimate of the current fill-volume of liquid (or other substance) within the relevant tank. In non-level operations, however, this conversion may not provide an appropriately accurate fill-volume. As such, method 200 may include determining 214 a tilt-corrected fill-volume based upon both the determined 212 fill-volume indicator and the determined 210 tilt value. For example, a polynomial (or other) model or related look-up table may be employed to utilize one or more determined 210 tilt values (e.g., vehicle pitch 204 and roll 206) in conjunction with the determined 212 fill-volume indicator, in order to determine 214 a tilt-corrected fill-volume. In certain implementations, an indicator of the determined 214 tilt-corrected fill-volume may then be provided 238 at an output interface (e.g., an output interface of the relevant computing device or a display device such as display 16).

Continuing, in certain embodiments, vehicle pitch 204 and vehicle roll 206 (e.g., as determined 210 based upon the determined 202 indicator of vehicle tilt) may be utilized separately in order to determine 214 a tilt-corrected fill volume. For example, a first numerical model (or look-up table) for the relevant tank, which may relate tank fill-volume to tank pitch (e.g., determined to be equal to vehicle pitch 204) and the determined 212 fill-volume indicator (e.g., a voltage indicating a height of a float sensor). Accordingly, this first model (or table) may be used to determine 216 a preliminary pitch-corrected estimate based upon the determined 210 vehicle pitch 204 and the determined 212 tank fill-volume indicator. Further, a second numerical model may represent the fill-volume error introduced by the determined 210 vehicle roll 206 (e.g., determined to be equal to tank roll), with respect to a fill-volume determined for level operation (e.g., as based upon the determined 212 fill-volume indicator). This second numerical model may accordingly be used to determine 218 a roll-based correction (i.e., error) based upon the determined 210 vehicle roll 206 and the determined 212 tank fill-volume indicator, which determined 218 roll-based correction may be subtracted 220 from the determined 216 pitch-corrected estimate to determine 214 a fill volume that has been corrected for both pitch 204 and roll 206.

Continuing, in an implementation using float sensor 32b for tank 12b, various coefficients ($C_i$) may be determined relating a percentage height (h) (i.e., a percent of maximum liquid height, as indicated by float 34b) and vehicle pitch ($\psi$) to a pitch-corrected fill-volume volume estimate, where h may be derived, for example, from a voltage signal from float sensor 32b. In a model that is fifth-order in h, and third order in $\psi$, therefore, the pitch-corrected estimate may be determined 216 as the scalar:

$$\begin{bmatrix} C_1 & C_2 & C_3 & C_4 & C_5 & C_6 \\ C_7 & C_8 & C_9 & C_{10} & C_{11} & C_{12} \\ C_{13} & C_{14} & C_{15} & C_{16} & C_{17} & C_{18} \\ C_{19} & C_{20} & C_{21} & C_{22} & C_{23} & C_{24} \end{bmatrix}.$$

$$\begin{bmatrix} h^5\psi^3 & h^4\psi^3 & h^3\psi^3 & h^2\psi^3 & h\psi^3 & \psi^3 \\ h^5\psi^2 & h^4\psi^2 & h^3\psi^2 & h^2\psi^2 & h\psi^2 & \psi^2 \\ h^5\psi & h^4\psi & h^3\psi & h^2\psi & h\psi & \psi \\ h^5 & h^4 & h^3 & h^2 & h & 1 \end{bmatrix}.$$

Likewise, various coefficients ($D_i$) may be determined relating the same percentage height (h) and vehicle roll ($\theta$) to a roll-based fill-volume correction. Again, in a model that is fifth-order in h, and third order in $\theta$, therefore, the roll-based correction may be determined 218 as the scalar:

$$\begin{bmatrix} D_1 & D_2 & D_3 & D_4 & D_5 & D_6 \\ D_7 & D_8 & D_9 & D_{10} & D_{11} & D_{12} \\ D_{13} & D_{14} & D_{15} & D_{16} & D_{17} & D_{18} \\ D_{19} & D_{20} & D_{21} & D_{22} & D_{23} & D_{24} \end{bmatrix} \cdot \begin{bmatrix} h^5\theta^3 & h^4\theta^3 & h^3\theta^3 & h^2\theta^3 & h\theta^3 & \theta^3 \\ h^5\theta^2 & h^4\theta^2 & h^3\theta^2 & h^2\theta^2 & h\theta^2 & \theta^2 \\ h^5\theta & h^4\theta & h^3\theta & h^2\theta & h\theta & \theta \\ h^5 & h^4 & h^3 & h^2 & h & 1 \end{bmatrix}.$$

Accordingly, pitch- and roll-corrected tank fill volume may be determined 214 as the scalar:

$$\begin{bmatrix} C_1 & C_2 & C_3 & C_4 & C_5 & C_6 \\ C_7 & C_8 & C_9 & C_{10} & C_{11} & C_{12} \\ C_{13} & C_{14} & C_{15} & C_{16} & C_{17} & C_{18} \\ C_{19} & C_{20} & C_{21} & C_{22} & C_{23} & C_{24} \end{bmatrix}.$$

-continued $$\begin{bmatrix} h^5\psi^3 & h^4\psi^3 & h^3\psi^3 & h^2\psi^3 & h\psi^3 & \psi^3 \\ h^5\psi^2 & h^4\psi^2 & h^3\psi^2 & h^2\psi^2 & h\psi^2 & \psi^2 \\ h^5\psi & h^4\psi & h^3\psi & h^2\psi & h\psi & \psi \\ h^5 & h^4 & h^3 & h^2 & h & 1 \end{bmatrix} -$$

$$\begin{bmatrix} D_1 & D_2 & D_3 & D_4 & D_5 & D_6 \\ D_7 & D_8 & D_9 & D_{10} & D_{11} & D_{12} \\ D_{13} & D_{14} & D_{15} & D_{16} & D_{17} & D_{18} \\ D_{19} & D_{20} & D_{21} & D_{22} & D_{23} & D_{24} \end{bmatrix}.$$

$$\begin{bmatrix} h^5\theta^3 & h^4\theta^3 & h^3\theta^3 & h^2\theta^3 & h\theta^3 & \theta^3 \\ h^5\theta^2 & h^4\theta^2 & h^3\theta^2 & h^2\theta^2 & h\theta^2 & \theta^2 \\ h^5\theta & h^4\theta & h^3\theta & h^2\theta & h\theta & \theta \\ h^5 & h^4 & h^3 & h^2 & h & 1 \end{bmatrix}.$$

It will be understood that a reversed approach may additionally (or alternatively) be employed, where roll 206 is utilized to determine 216 an initial roll-corrected estimate, and a pitch-based correction is determined 218 to adjust this determined 216 estimate to a determined 214 tilt-corrected fill-volume. Likewise, it will be understood that the fifth- and third-order models presented above are intended to be examples only, and that other models (or approaches, such as look-up tables) may be possible. It will also be understood that the value of h may be corrected or calibrated in various ways (e.g., through linear calibration based on known fill volumes), and that tank fill-volume indicators other than height (or percentage height) may be additionally (or alternatively) utilized. For example, weight or pressure measurements from a load cell or other device may be utilized in place of (or as a supplemental variable to) h, in the equations noted above (or others).

With an appropriate tilt-corrected fill volume having been determined 214, method 200 may also include controlling 222 various tank-filling, tank-mixing, spray application, or other spraying operations for sprayer 10 accordingly. As noted above, for example, various operations for sprayer 10 may include a primary fill operation and a secondary fill operation. For example, a carrier liquid may be pumped or otherwise fed into tank 12 during a primary fill operation (e.g., pumped or drained from a nurse truck or reservoir tank), with a variety of other substances diluted into the carrier liquid in a secondary fill operation. Because it may be important to precisely control the concentration of the final mixture, a PBSC method (e.g., method 200) may include providing 224 an indicator of the determined 214 tilt-corrected fill-volume after the primary fill operation, then receiving 226 an amount of substance in the secondary fill operation based upon the determined 214 tilt-corrected fill-volume. For example, method 200 may provide 224 an indicator of tilt-corrected fill volume to an operator via display 16, thereby allowing the operator to determine a precise amount of substance for the secondary fill operation. Additionally (or alternatively), after the primary fill operation, method 200 may include providing 224 an indicator of the determined 214 tilt-corrected fill-volume to a controller (e.g., controller 20). The controller may then automatically calculate the appropriate amount of substance for the secondary fill operation to guide an operator (e.g., by providing to the operator an indicator of the calculated amount for the secondary fill operation) and/or actively control the secondary fill operation to ensure that the appropriate amount of substance is added.

In certain implementations, method 200 may similarly include controlling 228 one or more pumping operations. For example, method 200 may control 228 a pumping operation for tank filling (or tank drainage) based upon a determined 214 tilt-corrected fill volume, in order to ensure that tank 12 includes an appropriate (or appropriately determined 214) amount of liquid during (and after) the pumping operation. Such control 228 may include various functions, including activating, deactivating, or otherwise regulating a pump, providing various indicators to an operator or other control system to facilitate pumping control, and so on.

Continuing, method 200 may include providing 230 an indicator of the determined 214 tilt-corrected fill volume to a material management (or other) system. For example, method 200 may communicate a tilt-corrected fill volume to a remote material management system in order to allow the remote system to accurately record and manage the distribution of various substances across an agricultural field (or otherwise). This, for example, may allow for relatively precise tracking and management of the use of various chemicals for appropriate program compliance, material tracking, and so on.

As will be appreciated by one skilled in the art, the disclosed subject matter may be embodied as a method, system, (e.g., a work vehicle control system included in sprayer 10) or computer program product. Accordingly, certain embodiments may be implemented entirely as hardware, entirely as software (including firmware, resident software, micro-code, etc.) or as a combination of software and hardware aspects. Furthermore, certain embodiments may take the form of a computer program product on a computer-usable storage medium having computer-usable program code embodied in the medium.

Any suitable computer usable or computer readable medium may be utilized. The computer usable medium may be a computer readable signal medium or a computer readable storage medium. A computer-usable, or computer-readable, storage medium (including a storage device associated with a computing device or client electronic device) may be, for example, but is not limited to, an electronic, magnetic, optical, electromagnetic, infrared, or semiconductor system, apparatus, or device, or any suitable combination of the foregoing. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device. In the context of this document, a computer-usable, or computer-readable, storage medium may be any tangible medium that can contain, or store a program for use by or in connection with the instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be non-transitory and may be any computer readable medium that is not a computer readable storage medium and that can communicate, propagate, or transport a program for use by or in connection with an instruction execution system, apparatus, or device.

Aspects of certain embodiments are described herein with reference to flowchart illustrations and/or block diagrams of methods, apparatus (systems) and computer program products according to embodiments of the invention. It will be understood that each block of any flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. Explicitly referenced embodiments herein were chosen and described in order to best explain the principles of the disclosure and their practical application, and to enable others of ordinary skill in the art to understand the disclosure and recognize many alternatives, modifications, and variations on the described example(s). Accordingly, various embodiments and implementations other than those explicitly described are within the scope of the following claims.

What is claimed is:

1. A computer-implemented method for controlling one or more operations of a sprayer vehicle, the sprayer vehicle including a tilt-detection mechanism, a tank, and a tank fill-volume sensor, the sprayer vehicle being disposed at a tilted orientation, the computer-implemented method comprising:
   determining, by the tilt-detection mechanism, one or more tilt indicators representing the tilted orientation of the sprayer vehicle;
   providing the determined one or more tilt indicators to one or more computing devices;
   determining, by the one or more computing devices, at least one tilt value based upon, at least in part, the determined one or more tilt indicators, the at least one tilt value representing a degree of tilt of at least one of the sprayer vehicle and the tank;
   determining, by the tank fill-volume sensor, fill-volume information for the tank;
   providing the fill-volume information to the one or more computing devices;
   determining, by the one or more computing devices, a tank fill-volume indicator based upon, at least in part, the fill-volume information from the tank fill-volume sensor;
   determining, by the one or more computing devices, a tilt-corrected fill-volume of the tank based upon, at least in part, the at least one tilt value and the tank fill-volume indicator;
   providing an indicator of the tilt-corrected fill-volume at an output interface, wherein the indicator of the tilt-corrected fill-volume is provided at the output interface after a primary fill operation; and
   determining, by the one or more computing devices, an amount of a secondary substance for a secondary fill operation, the amount of the secondary substance determined at least in part, by the provided indicator.

2. The computer-implemented method of claim 1, wherein the indicator of the tilt-corrected fill-volume is provided at the output interface after a primary fill operation, wherein the tank receives a primary substance during the primary fill operation and the indicator at the output interface indicates, at least in part, an amount of primary substance in the tank; and
   wherein the computer-implemented method further includes receiving an amount of secondary substance in a secondary fill operation, wherein the secondary substance is diluted by the primary substance, and the amount of secondary substance is determined based upon, at least in part, the determined tilt-corrected fill-volume provided by the indicator at the output interface.

3. The computer-implemented method of claim 2, wherein the secondary substance is at least one of an herbicide, a pesticide, and a fertilizer.

4. The computer-implemented method of claim 1, further comprising:
controlling a pumping operation for filling the tank based upon, at least in part, the determined tilt-corrected fill-volume provided by the indicator at the output interface.

5. The computer-implemented method of claim 1, wherein the at least one tilt value includes a pitch value of at least one of the vehicle and the tank, and a roll value of at least one of the vehicle and the tank.

6. The computer-implemented method of claim 1, wherein determining the tilt-corrected fill-volume includes:
determining a roll-corrected fill-volume estimate based upon, at least in part, the tank fill-volume indicator and a roll value;
determining a pitch-based fill-volume correction based upon, at least in part, the tank fill-volume indicator and a pitch value; and
subtracting the pitch-based fill-volume correction from the roll-corrected fill-volume estimate.

7. The computer-implemented method of claim 1, further comprising:
providing an indicator of the tilt-corrected fill-volume to a material-management system to manage one or more aspects of at least one of a tank-filling operation, tank mixing operation, and a spray-application operation.

8. The computer-implemented method of claim 1, wherein the tank fill-volume indicator is one or more of a height, a percentage height, a pressure, or a weight.

9. A computer-implemented method for controlling one or more operations of a sprayer vehicle, the sprayer vehicle including a tilt-detection mechanism, a tank, and a tank fill-volume sensor, the sprayer vehicle being disposed at a tilted orientation, the computer-implemented method comprising:
determining, by the tilt-detection mechanism, one or more tilt indicators representing the tilted orientation of the sprayer vehicle;
providing the determined one or more tilt indicators to one or more computing devices;
determining, by the one or more computing devices, at least one tilt value based upon, at least in part, the determined one or more tilt indicators, the at least one tilt value representing a degree of tilt of at least one of the sprayer vehicle and the tank;
determining, by the tank fill-volume sensor, fill-volume information for the tank;
providing the fill-volume information to the one or more computing devices;
determining, by the one or more computing devices, a tank fill-volume indicator based upon, at least in part, the fill-volume information from the tank fill-volume sensor;
determining, by the one or more computing devices, a tilt-corrected fill-volume of the tank based upon, at least in part, the at least one tilt value and the tank fill-volume indicator; and
providing an indicator of the tilt-corrected fill-volume at an output interface,
wherein the at least one tilt value includes a pitch value of at least one of the vehicle and the tank, and a roll value of at least one of the vehicle and the tank, and
wherein determining the tilt-corrected fill-volume includes:
determining a pitch-corrected fill-volume estimate based upon, at least in part, the tank fill-volume indicator and the pitch value;
determining a roll-based fill-volume correction based upon, at least in part, the tank fill-volume indicator and the roll value; and
subtracting the roll-based fill-volume correction from the pitch-corrected fill-volume estimate.

10. A control system for controlling one or more operations of a sprayer vehicle, the sprayer vehicle including a tilt-detection mechanism, a tank, and a tank fill-volume sensor, the control system comprising:
one or more processor devices; and
one or more memory architectures coupled with the one or more processor devices;
wherein the one or more processor devices are configured to:
determine one or more indicators of a tilt of the sprayer vehicle;
determine at least one tilt value based upon, at least in part, the determined one or more tilt indicators, the at least one tilt value representing a degree of tilt of at least one of the sprayer vehicle and the tank;
determine a tank fill-volume indicator based upon, at least in part, information from the tank fill-volume sensor;
determine a tilt-corrected fill-volume of the tank based upon, at least in part, the at least one tilt value and the tank fill-volume indicator;
provide an indicator of the tilt-corrected fill-volume after a primary fill operation, wherein the tank receives a primary substance during the primary fill operation and the tilt-corrected fill-volume indicates, at least in part, an amount of primary substance in the tank; and
determine an amount of secondary substance for a secondary fill operation, wherein the secondary substance is diluted by the primary substance, and the amount of secondary substance is determined based upon, at least in part, the determined tilt-corrected fill-volume.

11. The control system of claim 10, wherein the secondary substance is at least one of an herbicide, a pesticide, and a fertilizer.

12. The control system of claim 10, wherein the one or more processor devices are further configured to:
control a pumping operation for filling the tank based upon, at least in part, the determined tilt-corrected fill-volume.

13. The control system of claim 10, wherein the at least one tilt value includes a pitch value of at least one of the vehicle and the tank, and a roll value of at least one of the vehicle and the tank.

14. The control system of claim 13, wherein determining the corrected tank-level includes:
determining a pitch-corrected fill-volume estimate based upon, at least in part, the tank fill-volume indicator and the pitch value;
determining a roll-based fill-volume correction based upon, at least in part, the tank fill-volume indicator and the roll value; and
subtracting the pitch-based roll-volume correction from the pitch-corrected fill-volume estimate.

15. The control system of claim 13, wherein determining the corrected tank-level includes:
determining a roll-corrected fill-volume estimate based upon, at least in part, the tank fill-volume indicator and the roll value;
determining a pitch-based fill-volume correction based upon, at least in part, the tank fill-volume indicator and the pitch value; and
subtracting the pitch-based fill-volume correction from the roll-corrected fill-volume estimate.

16. The control system of claim 10, wherein the one or more processor
devices are further configured to:
provide an indicator of the tilt-corrected fill-volume of the tank to a material-management system to manage one or more aspects of at least one of a tank-filling operation, a tank-mixing operation, and a spray-application operation.

17. The control system of claim 10, wherein the tank fill-volume indicator is one or more of a height, a percentage height, a pressure, or a weight.

18. A sprayer vehicle comprising:
a tilt-detection mechanism configured to determine one or more tilt indicators representing a tilted orientation of the sprayer vehicle;
a tank;
a tank fill-volume sensor configured to determine fill-volume information for the tank; and
one or more controllers configured to:
receive the one or more tilt indicators from the tilt-detection mechanism;
determine at least one tilt value based upon, at least in part, the determined one or more tilt indicators, the at least one tilt value representing a degree of tilt of at least one of the sprayer vehicle and the tank;
receive the fill-volume information from the tank fill-volume sensor;
determine a tank fill-volume indicator based upon, at least in part, the fill-volume information;
determine a tilt-corrected fill-volume of the tank based upon, at least in part, the at least one tilt value and the tank fill-volume indicator;
provide, at an output interface, an indicator of the tilt-corrected fill-volume after a primary fill operation, wherein the tank receives a primary substance during the primary fill operation and the tilt-corrected fill-volume indicates, at least in part, an amount of primary substance in the tank;
determine an amount of secondary substance for a secondary fill operation, wherein the secondary substance is diluted by the primary substance, and the amount of secondary substance is determined based upon, at least in part, the determined tilt-corrected fill-volume; and
provide, at the output interface, an indicator of the determined amount of secondary substance.

* * * * *